(12) United States Patent
Horsmon et al.

(10) Patent No.: US 8,168,386 B1
(45) Date of Patent: May 1, 2012

(54) METHODS FOR DETECTING VENEZUELAN EQUINE ENCEPHALITIS VIRUS TC-83 AND ITS USE AS A BIOLOGICAL AGENT SIMULANT

(75) Inventors: Jennifer R. Horsmon, Parkville, MD (US); Kevin P. O'Connell, Abingdon, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 838 days.

(21) Appl. No.: 12/008,539

(22) Filed: Jan. 9, 2008

Related U.S. Application Data

(60) Provisional application No. 60/886,365, filed on Jan. 24, 2007.

(51) Int. Cl.
*C12Q 1/68* (2006.01)
*C12Q 1/70* (2006.01)
(52) U.S. Cl. .................... 435/6.12; 435/5; 435/6.15
(58) Field of Classification Search .................. None
See application file for complete search history.

(56) References Cited

OTHER PUBLICATIONS

Gen Bank Accession No. L10443 (available Nov. 2004).*
Linssen et al., "Development of Reverse Transcription-PCR Assays Specific for Detection of Equine Encephalitis Viruses," Journal of Clinical Microbiology, Apr. 2000, vol. 38, No. 4, pp. 1527-1535.*
O'Connell et al., "Real-Time Fluorogenic Reverse Transcription-PCR Assays for Detection of Bacteriophage MS2," Applied and Environmental Microbiology, Jan. 2006, vol. 72, No. 1, pp. 478-483.*
Aldea et al., "Rapid Detection of Herpes Simplex Virus DNA in Genital Ulcers by Real-Time PCR Using SYBR Green I Dye as the Detection Signal," Journal of Clinical Microbiology, Mar. 2002, vol. 40, No. 3, pp. 1060-1062.*
Lim et al., "Current and Developing Technologies for Monitoring Agents of Bioterrorism and Biowarfare," Clinical Microbiology Reviews, Oct. 2005, vol. 18, No. 4, pp. 583-607.*

* cited by examiner

*Primary Examiner* — Young J Kim
(74) *Attorney, Agent, or Firm* — Ulysses John Biffoni

(57) ABSTRACT

The present invention is generally related to products and methods that facilitate the use of Venezuelan equine encephalitis (VEE) virus TC-83 (TC-83) as a non-hazardous simulant, or surrogate, for viable pathogenic viruses. Specifically, TC-83 nucleic sequences are used in a method of detecting VEE or TC-83 in a sample thought to contain a biological threat agent. TC-83 and its nucleic acid sequence may therefore be used in the research, development, testing, evaluation, and training for technologies that enable the detection of biological threat agents. More particularly, specific primers and probes may be used to verify that instruments and systems using PCR detection methods are functioning properly.

10 Claims, 2 Drawing Sheets

METHODS FOR DETECTING VENEZUELAN EQUINE ENCEPHALITIS VIRUS TC-83 AND ITS USE AS A BIOLOGICAL AGENT SIMULANT

RELATED APPLICATION

This Application claims the benefit of priority from U.S. Provisional Application Ser. No. 60/886,365 filed on Jan. 24, 2007.

GOVERNMENT INTEREST

The invention described herein may be manufactured, used, and licensed by, or for the U.S. Government.

FIELD OF THE INVENTION

The present invention is generally related to products and methods that facilitate the use of Venezuelan equine encephalitis (VEE) virus TC-83 (TC-83) as a simulant, or surrogate, for viable pathogenic viruses. Specifically, TC-83 nucleic sequences are used in a method of detecting VEE or TC-83 in a sample thought to contain a biological threat agent. TC-83, and its nucleic acid sequence may, in turn, be used in the research, development, testing, evaluation, and training for technologies that enable the detection of biological threat agents.

BACKGROUND OF THE INVENTION

On Sep. 11, 2001, thousands lost their lives when the United States suffered a vicious and unprecedented attack. Shortly thereafter, the biological agent anthrax was sent through U.S. mail to government and media offices. Five Americans died. These attacks, while very different in scope and nature, exposed America's vulnerabilities to terrorists and biological weapons. In the case of biological weapons, the enemy is silent and often invisible. It is indiscriminate in choosing its victims, innocent people carrying out their daily routines. Anyone can become a victim and everyone is at risk.

The threat of biological warfare has existed for centuries. By definition, biological warfare involves any deliberate use of disease to attack humans, plants, animals, or infrastructure. Biological weapons have been used only occasionally, but they have the potential to inflict great harm. Unlike the materials necessary to produce nuclear weapons, microorganisms, toxins, and viruses that are dangerous to human, animal, and plant life can be found abundantly in nature. The technology needed to turn these agents into weapons is less sophisticated than what is necessary to develop nuclear weapons. Furthermore, only a very small quantity of material is needed, much less than that needed to produce nuclear weapons, but could potentially cause a comparable death-toll.

Technology allows for some biological threat agents, which in their natural state pose only minimal dangers, to be genetically engineered into more threatening forms. Their availability in nature also changes, and science continues to discover new biological threat agents. The Center for Disease Control (CDC) has compiled a list of the biological agents of greatest concern. They are segregated into three categories, depending on a variety of factors.

Though the need to develop biological defense technologies to protect against the threat of terrorism is increasing, such biological defense technologies are hard to develop and test. Biological defense technologies are successful if they are able to detect the biological threat agent, inhibit biological threat agent contact with its host, inhibit biological threat agent growth, or kill the biological threat agent Developing and testing biological defense technology in the presence of a biological threat agent poses serious hazards. Exposure of people, and the population at large, to a biological threat agent may result in serious injury or death. Methods allowing the safe development, testing, and training of biological defense technology are needed to minimize, or eliminate, the potential hazards associated with such technology development.

The most widely used methods in the safe development, testing and training of biological defense technology involve the use of simulants. A simulant is an agent having biological and/or physical characteristics similar to a biological threat agent but when used in place of the biological threat agent is not harmful. Though the use of methods involving simulants is a good idea, very few simulants have been identified and are being used.

SUMMARY OF THE INVENTION

Accordingly, it is an object of the present invention to meet the foregoing needs by providing safe methods for the development, testing and training of biological defense technology. One embodiment of the present invention is a method of testing biological detection systems by detecting an agent simulant in a sample, comprising: (a) contacting a nucleic acid sequence with a reagent comprising a forward primer comprising SEQ ID NO: 1, a reverse primer comprising SEQ ID NO: 2, a polymerase enzyme, and a nucleic acid probe comprising SEQ ID NO: 3, wherein a reporter and a quencher are attached to the probe comprising SEQ ID NO: 3; (b) amplifying the nucleic acid sequence; and (c) measuring the level of a detectable signal. It is preferred that the target nucleic acid sequence is amplified by thermal cycling. It is also preferred that the reporter is attached to the 5' end of, and the quencher is attached to the 3' end of, the probe comprising SEQ ID NO: 3. This configuration allows the quencher to substantially quench the reporter preventing the emission of the detectable signal when the nucleic acid probe is intact. During amplification, the nucleic acid probe is cleaved and then the reporter becomes substantially unquenched. In this manner biological detection systems which rely on PCR methods may be tested and evaluated without using hazardous biological threat agents.

Another embodiment of the present invention includes a method of detecting an agent in a sample, comprising: (a) contacting a nucleic acid sequence with a reagent comprising a forward primer, a reverse primer, a polymerase enzyme and SEQ ID NO: 3, wherein a reporter and a quencher are attached to SEQ ID NO: 3, (b) amplifying the nucleic acid sequence; and (c) measuring the level of a detectable signal. It is preferred that the nucleic acid sequence is amplified by thermal cycling.

Another embodiment of the present invention includes a method of testing biological detection systems by detecting an agent simulant in a sample, comprising: (a) contacting a nucleic acid sequence with a reagent comprising a forward primer comprising SEQ ID NO: 4, a reverse primer comprising SEQ ID NO: 5, a polymerase enzyme, and a nucleic acid probe comprising SEQ ID NO: 6, wherein a reporter and a quencher are attached to the probe comprising SEQ ID NO: 6; (b) amplifying the nucleic acid sequence; and (c) measuring the level of a detectable signal. It is preferred that the nucleic acid sequence is amplified by thermal cycling. It is also preferred that the reporter is attached to the 5' end of, and the quencher is attached to the 3' end of, probe comprising SEQ ID NO: 6. Based on this configuration, the quencher is capable of substantially quenching the reporter and preventing the emission of the detectable signal when the nucleic acid probe is intact.

Another embodiment of the present invention includes a method of detecting an agent, comprising: (a) contacting a nucleic acid sequence with a reagent comprising a forward primer, a reverse primer, a polymerase enzyme and SEQ ID NO: 6, wherein a reporter and a quencher are attached to the SEQ ID NO: 6; (b) amplifying the nucleic acid sequence; and (c) measuring the level of a detectable signal. It is preferred that the nucleic acid sequence is amplified by thermal cycling.

Another embodiment of the present invention is a method of detecting an agent, comprising: (a) contacting a nucleic acid sequence with a reagent comprising SEQ ID NO: 1 and SEQ ID: 2; (b) amplifying the nucleic acid sequence; and (c) measuring the level of a detectable signal. It is preferred that the nucleic acid sequence is amplified by thermal cycling. It is also preferred that the reagent further comprises a dye such as SYBR green; 5-carboxylfluorescein (5-FAM); tetrachloro-6-carboxyfluorescein; 6-carboxy-2'-4,7,7-tetrachlorofluorescein (6-TET), carboxy-X-rhodamine (ROX), 6-carboxy-4'-5'-dichloro-2',7'-dimethoxyfluorescein (JOE).

Another embodiment of the present invention is a method of detecting an agent, comprising: (a) contacting a nucleic acid sequence with a reagent comprising SEQ ID NO: 4 and SEQ ID: 5; (b) amplifying the nucleic acid sequence; and (c) measuring the level of a detectable signal. It is preferred that the nucleic acid sequence is amplified by thermal cycling. It is also preferred that the reagent further comprises a dye such as SYBR green; 5-carboxylfluorescein (5-FAM); tetrachloro-6-carboxyfluorescein; 6-carboxy-2'-4,7,7-tetrachlorofluorescein (6-TET), carboxy-X-rhodamine (ROX), 6-carboxy-4'-5'-dichloro-2',7'-dimethoxyfluorescein (JOE).

BRIEF DESCRIPTION OF THE DRAWINGS

The accompanying drawings, which are incorporated in and constitute a part of this specification, illustrate embodiments of the present invention and, together with the description, explain the advantages and principles of the invention.

DETAILED DESCRIPTION OF THE INVENTION

Figure 1:
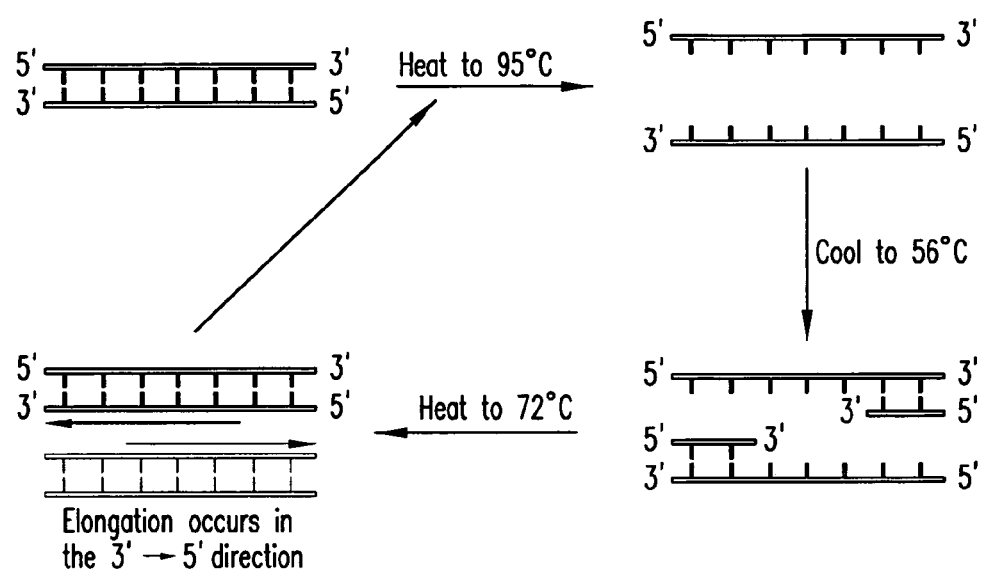
FIG. 1 A Diagram of a Standard PCR Amplification. A target nucleic acid is heated to a temperature enabling the separation of complementary strands or internal secondary structure. The target nucleic acid is then cooled in the presence of primers to allow annealing (or hybridizing) of primers to complementary sequences present in the target nucleic acid. DNA synthesis then occurs and the process is repeated a number of times.
Figure 2:
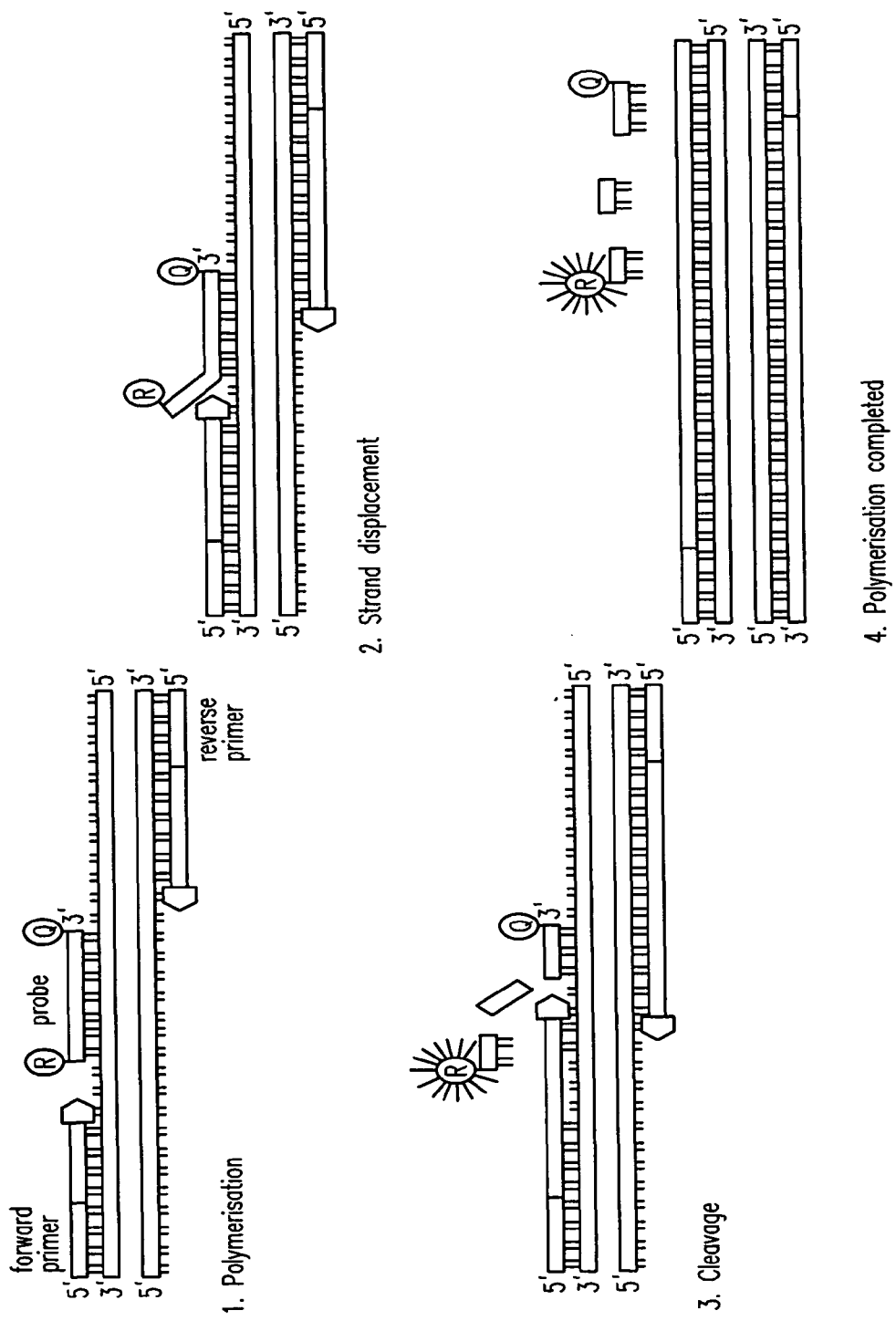
FIG. 2 A Diagram of a Real-Time Fluorescence PCR Amplification.

Reference will noW be made to preferred embodiments of this invention, examples of which will be obvious from the description of the invention. The current invention relates to: 1) methods and products used for the detection of biological threat agents; and 2) methods and products in which simulants (SEQ ID NUMBERS 1 through 6, or a combination thereof) replace biological threat agents (or nucleic acids thereof) during the development, testing and/or training of biological defense technology. In order to better understand the invention, the following terms have been defined.

The term "agent" means a biological threat agent or a combination thereof.

The term "biological defense technology" means a device, product and/or method able to detect a biological threat agent, or protect people, plants, livestock or other assets from contact with a biological threat agent, and/or render harmless or inactivate one or more biological threat agents. Examples of biological defense technology include detection systems such as those based on PCR technology, filters, masks, protective clothing, protective creams or gels, and decontamination products. A device includes a machine and/or equipment. A product includes a filter, gel, foam or other non-mechanical item. A method includes the use of a product and/or device.

The term "biological threat agent" means a microorganism or toxin that is dangerous or pathogenic to human, animal, and/or plant life. The term includes one or more biological threat agents and/or any combination of biological threat agents.

The term "harmful" means resulting in injury, disease or death.

The term "inactivate" means to kill cells, spores, viruses or toxins and render them harmless or nonviable.

The term "simulant" means an agent having similar biological and/or physical characteristics to a biological threat agent but when used in place of the biological threat agent is not harmful or pathogenic. The term includes one or more simulants and/or any combination of simulants.

The term "target nucleic acid sequence" refers to a nucleic acid sequence of VEE, whether it is derived from a virulent or non-virulent strain.

The term "TC-83" refers to Venezuelan equine encephalitis virus strain TC-83.

The term "VEE" refers to Venezuelan equine encephalitis.

A simulant of the present invention is one or more agent(s), such as a virus or a bacterium, which is safe when in contact with humans and is able to take the place of a biological threat agent, preferably during the development, testing, and training of biological defense technology. Such a simulant shall have similar characteristics, such as nucleic acid composition (such as an RNA or DNA genome), genome size, and form (such as enveloped or non-enveloped, Gram-positive or Gram-negative) as the biological threat agent it will replace.

A virus simulant of the present invention is TC-83, a vaccine strain of VEE. TC-83 of the present invention takes the place of the biological threat agent VEE, specifically the virulent, non-vaccine strains, during the safe development, testing, and training of biological defense technology. The present invention includes specific TC-83 nucleic acid sequences that are able to bind to itself (TC-83 nucleic acid sequences) and also to nucleic acids sequences of virulent strains of VEE. The reason for this is the TC-83 nucleic acid sequences of the present invention are identical, or nearly identical, to the nucleic acid sequence of some of the virulent strains of VEE.

One embodiment of the present invention is a method of detecting an agent, including a simulant (TC-83) or a virulent strain of VEE in a sample. By use of these methods, various PCR based biodetection systems may be tested and evaluated without actual use of the VEE virus, but through the use of primers and probes based on the non-virulent TC-83 strain. The method includes contacting target nucleic acid sequences present in a sample with one or more TC-83 nucleic acid sequence(s) or nucleic acid probes. It is preferred that real time fluorescence PCR is used to detect the presence of VEE in a sample, wherein one of the nucleic acid probes, includes a reporter attached to its 5' end, and a quencher attached to its 3' end or vice versa. After annealing the nucleic acid probes to one or more target nucleic acid sequences present in a sample, a polymerase chain reaction technique is used to amplifying a target nucleic acid sequence. The presence of a reporter and a quencher on a nucleic acid probe allows for the generation of a signal during an amplification process. The amount of signal corresponds to the amount of target nucleic acid sequence present in a sample, which corresponds to the amount of biological threat agent (i.e. specifically VEE) present in the sample. A brief description of the polymerase chain reaction method used in the present invention will now be described.
PCR As shown in FIG. 1, the target nucleic acid sequence is heated so that it becomes denatured to form single stranded nucleic acid sequences. The denatured nucleic acid sequences are cooled and nucleic acid probes are annealed. Taq polymerase binds the 3' end of each nucleic acid probe annealed to a target nucleic acid sequence and extends each of these primers in the 5' to 3' direction along the target nucleic acid sequence. PCR typically results in a doubling of the number of copies of target nucleic sequence after each round of DNA synthesis, and a geometric increase in number of copies after each reaction cycle. The nucleic acid probes used in the present invention are TC-83 nucleic acid sequences. The PCR product (amplified target nucleic acid sequence) can be observed afterwards by separation of the DNA by agarose gel electrophoresis.

Real-Time Fluorescent PCR

In another aspect of the present invention, the nucleic acid probes may further include a reporter and a quencher each attached to the oligonucleotide as shown in FIG. 2. During PCR, the modified probe is designed to generate a detectable signal to indicate that it has hybridized with the target nucleic acid sequence. The reporter is a molecule, typically a dye, which can generate a detectable signal (e.g., fluorescence), and the quencher is a molecule which when placed in close proximity to the reporter is capable of substantially reducing or quenching the intensity of the detectable signal.

As long as both the reporter and the quencher are on the nucleic acid probe, the quencher inhibits the emission of a detectable signal by the reporter. However, as the polymerase extends the primer during amplification, the intrinsic 5' to 3' nuclease activity of the polymerase degrades the probe, separating the reporter from the quencher, and allowing the detectable signal to be emitted. Generally, the amount of detectable signal generated during the amplification cycle is proportional to the amount of product generated in each cycle.

As used herein, the terms "quenching" refer to the process whereby when a reporter and a quencher are in close proximity, and the reporter is excited by an energy source, a substantial portion of the energy of the excited state non-radioactively transfers to the quencher where it either dissipates non-radioactively or is emitted at a different emission wavelength than that of the reporter.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, it has been assumed that the reporter and the quencher be preferably attached to the probe within a few nucleotides of one another, usually with a separation of from about 6 to 16 nucleotides. Typically, this separation is achieved by attaching one member of a reporter-quencher pair to the 5' end of the probe and the other member to a base 6 to 16 nucleotides away.

Preferably, the reporter is selected from fluorescent organic dyes modified with a suitable linking group for attachment to the terminal 3' carbon or terminal 5' carbon of the probe via a linking moiety. The quencher is selected from organic dyes, which may be fluorescent, depending on the embodiment of the present invention. Generally, the absorption band of the quencher should at least substantially overlap the emission band of the reporter to optimize quenching. Non-fluorescent quenchers or dark quenchers typically function by absorbing energy from excited reporters, but do not release the energy radioactively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, 1971, In: Handbook of Fluorescence Spectra of Aromatic Molecules, 2nd ed., Academic Press, New York. Examples illustrating modifications to reporters and quenchers for covalent attachment via common reactive groups that can be added to an oligonucleotide in the present invention may be found in, e.g., Haugland, 1992, In: Handbook of Fluorescent Probes and Research Chemicals, Molecular Probes, Eugene, Oreg., the content of which is incorporated herein by reference.

Preferred reporters are xanthene dyes including fluoresceins and rhodamine dyes. Many suitable forms of these compounds are available commercially with substituents on their phenyl groups, which can be used as the site for bonding or as the bonding functionality for attachment to an oligonucleotide. Another preferred group of fluorescent compounds for use as reporters are naphthylamines, having an amino group in the alpha or beta position. Included among such naphthylamino compounds are 1-demethylaminonaphthyl-5 sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine acridine orange; N-(p-(2-benzoxazolyl)phenyl)maleimide; benzoxadiazoles, stilbenes, pyrenes, and the like. Most preferably, the reporters are selected from fluorescein and rhodamine dyes. These dyes and appropriate linking methodologies for attachment to oligonucleotides are well known in the art.

Suitable examples of quenchers include those selected from 6-carboxy-tetramethylrhodamine, 4-(4-dimethylaminiophenylazo)benzoic acid (DABYL), tetramethylrhodamine (TAMRA), BHQ-0™, BHQ-2™, and BHQ-3™, each of which are available from Bioresearch Technologies, Inc., of Novato, Calif., QSY-7™, QSY-9™, QSY-21™ and QSY-35™, each of which are available from Molecular Probes, Inc., and the like. Additional examples of quenchers that may be used in the present invention include those selected from dyes such as SYBER® green, 5-carboxyfkluorescein (5-FAM™) available from Applied Biosystems of Foster City, Calif., tetrachloro-6-carboxyfluorescein, 6-carboxy-2'-4,7,7'-tetrachlorofluorescein (6-TET™) available from Applied Biosystems, carboxy-X-rhodamine (ROX), 6-carboxy-4'-5'-dichloro-2',7'-dimethoxyfluorescein (JOE™) available from Applied Biosystems, VIC™ dye products available from Molecular Probes, Inc., NED™ dye products available from Applied Biosystems, and the like.

In one embodiment of the present invention, a reporter is attached at the 5' end of the probe, with the reporter selected from fluoresceins such as 6-carboxyfluorescein (6-FAM) and a quencher selected from rhodamines such as 6-carboxy-tetramethyl-rhodamine (TAMRA) which may be attached to any T position or at the 3' end thereof as described in Livak et al., "Guidelines for Designing TaqMan™ Fluorogenic Probes for 5' Nuclease Assays," found in Perkin-Elmer Research News, 1995, Applied Biosystems Division of Foster City, Calif., the content of which is incorporated herein by reference. Preferably, the nucleic acid probe (i.e. associated with the reporter and the quencher) may be adapted to have a higher melt temperature ($T_m$) than the other nucleic acid probes (i.e. used as primers for PCR) used in the present invention to amplify the target nucleic acid sequence. During the extension phase, the nucleic acid probe (i.e. associated with the reporter and the quencher) is at least substantially hybridized to the target nucleic acid sequence.

It will be understood that based on this disclosure the present invention is not limited to this particular reporter-quencher pair or the particular linkages used to attach the molecules to the probe. Rather, as previously discussed herein, a range of reporter-quencher pairs may be attached to the nucleic acid probe through various linkages as known to the skilled artisan. Further, the reporter-quencher pair need not be located on nucleotides which are immediately adjacent, instead, the quencher may be attached to any nucleotide on the nucleic acid probe and still quench the emission of the reporter attached to the 5' end thereof.

Discussion will now focus on examples of using the detection technology of the present invention. It is possible using the present invention to detect biological threat agent(s) in the air, in water, or on solid surfaces. Detection of such agent(s) in air generally consists of three steps: sample collection; sample processing; and sample analysis. Instrumentation accomplishing each step may be part of an integrated systems. Alternatively, samples may be collected, processed, and analyzed by separate systems (or by humans working with laboratory equipment). Some detection systems may sample the air passively, using currents in ambient air to cause airborne agents to move into the portion of the device that performs the analysis (in much the same way as a smoke detector detects smoke particles only when particle-laden air wafts into the interior of the detector).

Most samplers that draw agents from air exploit one or more physical characteristics of the agents targeted for collection and contact with the biological defense technology. Such methods include but are not limited to: the use of filters (separation of particles from air based on size). Air can be drawn by fans (or other methods of moving air) and passed through filters designed with pore sizes small enough to retard the passage of airborne particles that carry virions. Another class of samplers, accelerates air (and therefore airborne agents), and increases the momentum of airborne agents, then passes such particles through a path in the instrument in such a way that the momentum of particles causes them to leave the airstream and impact on a surface or into a fluid where they are arrested. Such devices are often said to work by "impaction" and may be called an "impaction sampler". Conceivably, air samplers for biological threat agents could also work by adsorption (an adsorption sampler), in which air is passed through a column filled with a porous substrate that has an affinity for the biological threat agents based on one or more methods, including but not limited to: charge, the complementarity of molecular surface structures (including but not limited to an antibody-antigen interaction), relative hydrophobicity/hydrophilicity. Sample collection from liquid samples employs many of the same techniques listed above.

Sample collection from surfaces usually employs the use of a swab (often composed of cotton, but can be any of a large number of materials) or other material or device that is wiped over a surface with the intent that particles on the surface adhere to the swab.

The term "sample processing" refers to methods of preparing a sample for analysis, which is making the biological threat agent or components thereof such as membrane proteins, DNA, and/or RNA accessible (able to come in contact with) to a detection device so that the detection device is able to detect the presence of a molecule characteristic to a biological threatening agent. Such molecules include RNA, DNA, protein and/or lipid (i.e., content and/or composition). Typically, the integrity of a biological threat agent's cell, spore, or virion is disrupted by chemical, enzymatic, electrical, mechanical and/or other means. For example, such disruption means may cause the release of nucleic acids from a biological threat agent and make them available for methods of analysis that rely upon nucleic acid sequence information for detection and identification. Another reason a sample might require preparation is that a molecule characteristic of a biological threat agent may have to be modified or combined with other compounds before analysis. An example of this kind of modification is the derivatization of small molecules before gas chromatographic analysis.

Some biological defense technology must be able to detect very small amounts of biological threat agents in a relative large amount of material; for example, a small number of anthrax spores in a thick layer of dust on top of a computer. Such non-pathogenic material collected with a biological threat agent must be removed before a biological threat agent may be detected and identified. Methods for the removal of such non-pathogenic materials may include, but are not limited to, purification by means of ligand-receptor affinity (of which antibody-antigen affinity is but one possible example).

Some biological defense technology is able to protect people, plants, livestock or other assets from contact with a pathogen. Such biological defense technologies include devices, products and/or methods that create a barrier between the biological threat agent and the person, plant or livestock. The goal is that a biological threat agent is able to contact the biological defense technology but is unable to penetrate such technology. Such biological defense technology includes, but is not limited to, filters (either on a mask for an individual, or on a ventilation system that protects a building, temporary shelter, or vehicle), clothing that has pore sizes small enough to prevent the deposition and penetration of biological threat agent-bearing particles onto the skin, creams that form a barrier between skin and ambient air and may trap and inactivate a biological threat agent in airborne particles (in which case such a technology would both protect and decontaminate). During testing of a biological defense technology, a simulant may be placed in contact with a biological defense technology and then detection tests are performed to determine whether or not a simulant is able to penetrate the barrier of the biological defense technology. If the simulant is observed to penetrate the barrier of the biological defense technology, then the biological defense technology is modified to prevent such penetration or contact with humans.

Examples of biological defense technology used after an intentional or naturally occurring contamination (i.e. decontamination technology) include devices, products and methods that are able to inactivate or kill cells, spores or virions of a biological threat agent, and render them harmless or non-viable. Such technologies include but are not limited to chemical solutions that contain compounds that disrupt cell, spore, or virion structural integrity, chemically modify cellular, spore, or viral small molecules or macromolecules so that they no longer perform their essential biochemical functions, or modify, inactivate, or mask molecules or structures on the surfaces of a biological threat agent cells, spores, or virions so that they no longer interact with host cells or tissues in such a way as to lead to disease.

Other types of decontamination technologies include but are not limited to methods and devices that transmit radiant energy (such as ultraviolet radiation) to biological threat agent cells, spores, or virions in such a way that the absorbance of the radiant energy disrupts biological threat agent cells, spores, or virions in the ways mentioned above. Another class of decontamination technology includes methods or devices that generate aerosols or gaseous emissions of substances that inactivate biological threat agent cells, spores, or virions in the ways described above. An example of such a technology is a vaporous hydrogen peroxide (VHP) generator. Hydrogen peroxide vapors, chlorine dioxide, paraformaldehyde vapors, or combinations thereof, are capable of penetrating the interiors of equipment and destroying biological threat agent cells by chemically (oxidatively or otherwise) modifying small or macromolecules of biological threat agent cells, spores, or virions so that they are no longer viable or able to cause disease.

EXAMPLES

Example 1

Detection By PCR

Sequences from the whole genome sequence of VEE strain TC-83 (GenBank accession number L01443) were used to develop assays for the specific detection of VEE strain TC-83. Candidate probe and primer sequences were designed with Primer Express 2.0 software (Applied Biosystems, Foster City, Calif.). Primer sequences were analyzed for specificity by comparison with known gene sequences by using the National Center for Biotechnology Information GenBank database with the BLAST search tool. The oligonucleotide primer and probe sets selected are as follows:

Forward primer 1:
[SEQ ID NUMBER:1] 5'-CATGAGGCACATCTTG-GAGAGA-3'

Reverse primer 1:
[SEQ ID NUMBER:2] 5'-CCCAACACACGTTTGC-CTTA-3'

Probe sequence 1:
[SEQ ID NUMBER:3] 5'-[FAM]-CGGACCCTAC-CGACGTCTTCCAGA-[TAMRA]-3'

Forward primer 2:
[SEQ ID NUMBER:4] 5'-CACCTCGTGGCT-TGATAAAGG-3'

Reverse primer 2:
[SEQ ID NUMBER:5] 5'-CGGAGAAAGCACAGCG-TAAGA-3'

Probe sequence 2:
[SEQ ID NUMBER:6] 5'-[FAM]-TACCAGCTACGATG-GCGAGGACAAGATC-[TAMRA]-3'

These nucleic acid probe sequences permit one skilled in the art to detect two separate target sequences in the TC-83 genome or the genomes of closely related strains of VEE. With each primer pair is listed the nucleic acid probe sequence. Each probe must be ordered synthesized from a commercial vendor with the dye and quencher molecules incorporated into the synthesis.

The nucleic acid probe sets are used in each PCR assay to detect the presence of TC-83 genomic RNA. Primers were synthesized by Integrated DNA Technology, Inc. (Coralville, Iowa) and 5' 6-carboxy-fluorescein (FAM), 3'-carboxymethylrhodamine (TAMRA)) were purchased from Applied Biosystems.

Example 2

Detection by Nucleic Acid Hybridization

In addition to PCR, other methods based on the use of complementary nucleic acid probe sequences can be used in the present invention to detect the presence of TC-83 genomic RNA. Such methods include but are not limited to Northern blotting, in which nucleic acids in a sample are digested with restriction endonucleases and separated by electrophoresis in an agarose gel. The restriction fragments so generated are transferred to a nylon membrane by blotting. A probe consisting of nucleic acids complementary to TC-83 nucleic acid sequences is labeled with radioisotopes or a small molecule (such as digoxigenin) or other labels. The labeled probe is placed with the blot in solution that permits the probe to hybridize specifically with complementary TC-83 genomic RNA sequences, if present on the blot. After hybridization, unbound probe is washed away, and the presence of bound probe (indicative of the presence of VEE strain TC-83 genomic RNA in the original sample) is detected by autoradiography (if the labeled with radioisotope) or a chromogenic biochemical reaction (if the probe is labeled with small molecule for which an enzyme-linked anti-label antibody is available), or other label-specific detection method.

All patent, patent applications, and publications mentioned are incorporated by reference in their entirety into this application.

REFERENCES a) Sambrook, J., E. F. Fritsch, and T. Maniatis. 1989. Molecular Cloning: a Laboratory Manual, 2nd ed. Cold Spring Harbor Laboratory Press, Cold Spring Harbor, N.Y.

Bartlett J. M. S., Stirling D., eds. 2003. PCR Protocols, $2^{nd}$ ed. (Volume 226 in the series Methods in Molecular Biology.) Humana Press, Totowa, N.J.

The foregoing description of embodiments of the present invention provides an exemplary illustration and description, but is not intended to be exhaustive or to limit the invention to the precise form disclosed. Modifications and variations are possible in light of the above teachings or may be acquired from practice of the invention. One skilled in the art will recognize that various changes, modifications, and variations can be made without departing from the spirit and scope of the invention as defined in the following claims.

What is claimed is:

1. A method of testing biological detection systems by detecting an agent simulant in a sample, comprising:
   (a) contacting a nucleic acid sequence with a reagent consisting of a forward primer consisting of SEQ ID NO: 1, a reverse primer consisting of SEQ ID NO: 2, a polymerase enzyme, and a nucleic acid probe consisting of SEQ ID NO: 3, wherein a reporter and a quencher are attached to the probe consisting of SEQ ID NO: 3;
   (b) amplifying the nucleic acid sequence; and
   (c) measuring the level of a detectable signal.

2. The method of claim 1, wherein the nucleic acid sequence is amplified by thermal cycling.

3. The method of claim 1, wherein the reporter is attached to the 5' end of said probe consisting of SEQ ID NO: 3.

4. The method of claim 1, wherein the quencher is attached to the 3' end of said probe consisting of SEQ ID NO: 3.

5. The method of claim 1, wherein the quencher is capable of substantially quenching the reporter preventing the emission of the detectable signal when the nucleic acid probe is intact.

6. The method of claim 1, wherein the reporter becomes substantially unquenched when the nucleic acid probe is cleaved during amplification.

7. A method of detecting Venezuelan Equine Encephalitis TC-83, comprising;
   (a) contacting a nucleic acid sequence with a reagent consisting of SEQ ID NO:1, and SEQ ID:2;
   (b) amplifying the nucleic acid sequence; and
   (c) measuring the level of a detectable signal.

8. The method of claim 7, wherein the nucleic acid sequence is amplified by thermal cycling.

9. The method of claim 7, wherein the reagent further comprises a dye.

10. The method of claim 9, wherein the dye is selected from the group consisting of SYBR green; 5-carboxylfluorescein (5-FAM); tetrachloro-6-carboxyfluorescein; 6-carboxy-2'-4,7,7-tetrachlorofluorescein (6-TET), carboxy-X-rhodamine (ROX), 6-carboxy-4'-5'-dichloro-2',7'-dimethoxyfluorescein (JOE).

* * * * *

SEQUENCE LISTING

<160> NUMBER OF SEQ ID NOS: 6

<210> SEQ ID NO 1
<211> LENGTH: 22
<212> TYPE: DNA
<213> ORGANISM: Artificial Sequence
<220> FEATURE:
<223> OTHER INFORMATION: Description of Artificial Sequence: Synthetic primer -continued

<400> SEQUENCE: 1
catgaggcac atcttggaga ga                                          22

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cccaacacac gtttgcctta                                             20

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
cggaccctac cgacgtcttc caga                                        24

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cacctcgtgg cttgataaag g                                           21

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cggagaaagc acagcgtaag a                                           21

<210> SEQ ID NO 6
<211> LENGTH: 28
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
taccagctac gatggcgagg acaagatc                                    28